United States Patent [19]

Kubo

[11] Patent Number: 4,519,237
[45] Date of Patent: May 28, 1985

[54] OXYGEN-SENSING SYSTEM

[75] Inventor: Hiromasa Kubo, Yokohama, Japan

[73] Assignee: Nissan Motor Company, Limited, Yokohama, Japan

[21] Appl. No.: 545,696

[22] Filed: Oct. 26, 1983

[30] Foreign Application Priority Data

Oct. 30, 1982 [JP] Japan .............................. 57-189993

[51] Int. Cl.³ ........................................... G01N 27/12
[52] U.S. Cl. ........................................ 73/23; 123/440
[58] Field of Search ............... 73/23, 27 R; 123/440, 123/489; 60/276, 285; 364/497, 424; 422/98

[56] References Cited

U.S. PATENT DOCUMENTS

| 4,094,186 | 6/1978 | Wessel | 73/23 |
| 4,147,513 | 4/1979 | Bienkowski et al. | 73/23 |
| 4,258,563 | 3/1981 | Yasuda et al. | 73/23 |
| 4,306,444 | 12/1981 | Hattori et al. | 73/23 |
| 4,462,374 | 9/1984 | Kobayashi et al. | 123/440 |

Primary Examiner—Stephen A. Kreitman
Attorney, Agent, or Firm—Schwartz, Jeffery, Schwaab, Mack, Blumenthal & Evans

[57] ABSTRACT

A sensing element exposed to a gas to be analyzed has an internal resistance which depends on its temperature and also on the oxygen concentration in the gas. A thermistor has an internal resistance which depends on its temperature. The thermistor is positioned near the sensing element so that the temperature of the thermistor substantially coincides with the temperature of the sensing element. The ratio of the internal resistances of the thermistor and the sensing element is substantially independent of the temperature of the thermistor and the sensing element but is dependent on the oxygen concentration in the gas. A first device serves to sense the internal resistance of the thermistor and thereby determine the temperature of the sensing element. A second device serves to sense the ratio of the internal resistances of the thermistor and the sensing element and thereby determine the oxygen concentration in the gas. At first, the first device is enabled and the second device is disabled. When the determined temperature of the sensing element rises to a predetermined reference level, the first device is disabled and the second device is enabled.

6 Claims, 9 Drawing Figures

OXYGEN-SENSING SYSTEM

BACKGROUND OF THE INVENTION

This invention relates to a system for sensing oxygen, e.g., which can be used in mixture air-to-fuel ratio control for an internal combustion engine.

It is known to regulate the air-to-fuel ratio of an air/fuel mixture at and around an optimal level by means of a closed-loop or feed-back control system in an internal combustion engine. This closed-loop control system has an oxygen sensor for sensing the oxygen concentration in exhaust gases which represents the mixture air-to-fuel ratio.

Oxygen sensors using titanium dioxide as sensing elements have been recently developed. The internal impedance or resistance of this titania sensor varies as a function of the oxygen concentration in ambient gas.

The internal impedance or resistance of the titania sensor also depends on the temperature thereof. Specifically, the impedance or resistance increases exponentially with decreases in temperature. Accordingly, the titania sensor needs temperature compensation for reliability. When the temperature is lower than a certain value, however, the accuracy or reliability of the titania sensor remains unacceptable regardless of the temperature compensation, since the impedance or resistance thereof is excessively high. The accuracy or reliability remains acceptable at temperatures above that certain value.

In the case where such a titania sensor is used in the closed-loop engine mixture control system, it is desirable to disable or suspend the closed-loop control and regulate the air-to-fuel ratio in another way, such as an open-loop control, when the temperature of the sensor remains within an inoperative or inactive range in which its accuracy or reliability is unacceptable. Such a function necessitates a determination of whether or not the temperature of the sensor is within the inoperative range. Proposed control circuits for effecting this function including the temperature determination have been unsatisfactory, since they tend to degrade the accuracy or reliability of the titania sensor especially at temperatures slightly above the inoperative range.

SUMMARY OF THE INVENTION

Accordingly, it is an object of this invention to provide an oxygen-sensing system which can accurately determine whether or not the temperature of the sensor is within an inoperative range without degrading the accuracy or reliability thereof.

In accordance with this invention, a sensing element exposed to a gas to be analyzed has an internal resistance which depends on its temperature and also on the oxygen concentration in the gas. A thermistor has an internal resistance which depends on its temperature. The thermistor is positioned near the sensing element so that the temperature of the thermistor substantially coincides with the temperature of the sensing element. The ratio of the internal resistances of the thermistor and the sensing element is substantially independent of the temperature of the thermistor and the sensing element but is dependent on the oxygen concentration in the gas. A first device serves to sense the internal resistance of the thermistor and thereby determine the temperature of the sensing element. A second device serves to sense the ratio of the internal resistances of the thermistor and the sensing element and thereby determine the oxygen concentration in the gas. Preferably, the first device is enabled and the second device is disabled at first. When the determined temperature of the sensing element rises to a predetermined reference level, the first device is disabled and the second device is enabled.

The above and other objects, features and advantages of this invention will be apparent from the following description of preferred embodiment thereof, taken in conjunction with the drawings.

BRIEF DESCRIPTION OF THE DRAWINGS

Like parts, signals, and voltages are denoted by like reference numerals and characters throughout the drawings.

DESCRIPTION OF THE PREFERRED EMBODIMENTS

Figure 1:
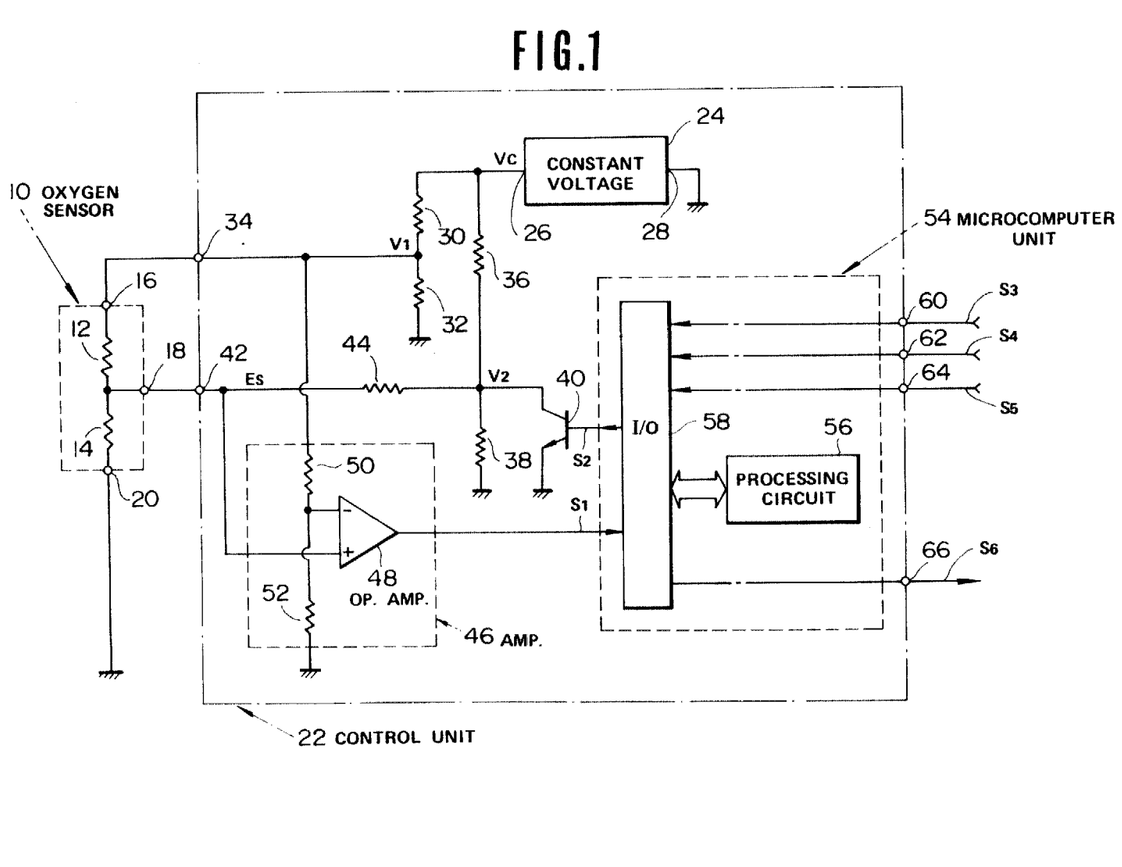
FIG. 1 is a schematic diagram of an oxygen-sensing according to a first embodiment of this invention.

With reference to FIG. 1 diagrammatically illustrating a first embodiment of this invention, an oxygen sensor 10 includes a series combination of an sensing element 12 and a thermistor 14. The oxygen sensor 10 also includes first, second, and third terminals 16 18, and 20. One end of the sensing element 12 is connected to the first terminal 16 and the other end thereof is connected to the second terminal 18. One end of the thermistor 14 is connected to the second terminal 18 and the other end thereof is connected to the third terminal 20. Thus, the junction between the sensing element 12 and the thermistor 14 is connected to the second terminal 18.

The sensing element 12 is made of an oxide semiconductor, such as a titanium dioxide ceramic. The internal impedance or resistance of the sensing element 12 varies as a function of the oxygen concentration in the ambient gas. As shown by the curves A and C in FIG. 2, the internal resistance of the sensing element 12 exponentially increases as its temperature drops. The characteristic curves A and C are obtained when the oxygen sensor 10 is placed in excess- and reduced-oxygen environments, respectively. The internal resistances of the oxygen sensor 10 placed in an excess-oxygen environment are considerably greater than those of the oxygen sensor 10 placed in a reduced-oxygen environment at equal temperatures. For temperature compensation, the thermistor 14 is designed so that the internal resistance of the thermistor 14 will vary with temperature along the curve B in FIG. 2 similar in form to the curves A and C. In other words, the resistance-temperature characteristic curve B of the thermistor 14 is designed so as to have a form or configuration analogous to that of the characteristic curves A and C of the sensing element 12. This design ensures that the ratio of the internal resistances of the thermistor 14 and the sensing element 12 will be independent of the temperature of the oxygen sensor 10. In addition, the thermistor 14 is preferably designed to have an internal resistance which is substantially centered between the internal resistances of the sensing element 12 in excess- and reduced-oxygen environments at all temperatures.

The oxygen sensor 10 is mounted in the exhaust system of an internal combustion engine (not shown) in such a manner that the sensing element 12 will be exposed to exhaust gases emitted from the combustion chambers of the engine. Thus, the sensing element 12 will be responsive to the oxygen concentration in the exhaust gases which represents the air-to-fuel ratio of the air/fuel mixture drawn into the combustion chambers of the engine. The thermistor 14 is located near the sensing element 12 so that the temperature of the thermistor 14 will always coincide with that of the sensing element 12 for reliable temperature compensation. This temperature of the thermistor 14 or the sensing element 12 is defined as the temperature of the oxygen sensor 10.

A control circuit 22 includes a constant-voltage source or a constant-voltage supply circuit 24 acting to generate a preset constant DC voltage Vc. The voltage source 24 has a pair of positive and negative output terminals 26 and 28. The negative output terminal 28 of the voltage source 24 is grounded. The positive output terminal 26 of the voltage source 24 is connected to one end of a voltage-dividing series combination of resistors 30 and 32. The other end of this resistor combination is grounded. This resistor combination serves to divide the constant voltage Vc. The control circuit 22 includes a first terminal 34, to which the junction between the resistors 30 and 32 is connected. This terminal 34 is connected to the terminal 16 of the oxygen sensor 10. The third terminal 20 of the oxygen sensor 10 is grounded. Thus, the voltage $V_1$ across the resistor 32 resulting from dividing the constant voltage Vc is supplied across the series combination of the sensing element 12 and the thermistor 14 of the oxygen sensor 10.

One end of another voltage-dividing series combination of resistors 36 and 38 is connected to the positive output terminal 26 of the voltage source 24, and the other end of this resistor combination is grounded. The collector of an NPN transistor 40 is connected to the junction between the resistors 36 and 38. The emitter of the transistor 40 is grounded. This transistor 40 serves to controllably short-circuit the resistor 38. The combination of the resistors 36 and 38 serves to divide the constant voltage Vc, provided that the transistor 40 is nonconductive. The control circuit 22 includes a second terminal 42, to which one end of a resistor 44 is connected. The other end of the resistor 44 is connected to the junction between the resistors 36 and 38. The terminal 42 is connected to the terminal 18 of the oxygen sensor 10. Thus, the resistor 44 is connected in series with the thermistor 14. The voltage $V_2$ across the resistor 38 resulting from dividing the constant voltage Vc is supplied across the series combination of the thermistor 14 and the resistor 44. This voltage $V_2$ is chosen to be higher than the voltage $V_1$ across the resistor 32 when the transistor 40 is nonconductive.

An amplifier 46 includes an operational amplifier 48 and resistors 50 and 52. The inverting input terminal of the operational amplifier 48 is connected to the junction between the resistors 30 and 32 via the resistor 50, and is grounded via the resistor 52. The noninverting input terminal of the operational amplifier 48 is connected to the terminal 42. The amplifier 46 serves to linearly magnitude the voltage Es across the thermistor 14 which can represent either the oxygen concentration in the exhaust gas, that is, the air-to-fuel ratio of the air/fuel mixture, or the temperature of the oxygen sensor 10, as described hereinafter. The amplifier 46 may act as a buffer only. In response to the voltage Es, the amplifier 46 generates a signal $S_1$ having a voltage proportional to the voltage Es and thus representing either the air-to-fuel ratio of the mixture or the temperature of the oxygen sensor 10.

A digital microcomputer unit 54 includes a processing or operational circuit 56 and an input/output (I/O) circuit 58 connected to the processing circuit 56. The processing circuit 56 has a central processing unit (CPU), a read-only memory (ROM) connected to the CPU, and a random-access memory also connected to the CPU. The microcomputer unit 54 operates in accordance with a program stored in the ROM of the processing circuit 56. The I/O circuit 58 is connected to the output terminal of the operational amplifier 48 to receive the signal $S_1$. The I/O circuit 58 includes an analog-to-digital converter for converting the analog signal $S_1$ into a corresponding digital signal, from which the processing circuit 56 derives a digital value indicative of the voltage of the analog signal $S_1$. The microcomputer unit 54 outputs a signal $S_2$ via the I/O circuit 58 on the basis of the signal $S_1$. The base of the transistor 40 is connected to the I/O circuit 58 to receive the signal $S_2$, which is designed to control the transistor 40. Specifically, the signal $S_2$ assumes either a low level or a high level. When the signal $S_2$ assumes the low level, the transistor 40 goes nonconductive. When the signal $S_2$ assumes the high level, the transistor 40 goes conductive, thereby short-circuiting the resistor 38.

The control circuit 22 includes third, fourth, and fifth terminals 60, 62, and 64. The third terminal 60 receives an ignition-pulse or crank-angle signal $S_3$ produced on the basis of the output of a well-known crank angle sensor (not shown). The third terminal 60 is connected to the I/O circuit 58 to transmit the ignition signal $S_3$ to the I/O circuit 58. The I/O circuit 58 includes a frequency detector, which monitors the frequency of the ignition signal $S_3$ and generates a digital signal indicative thereof. Since the frequency of the ignition signal $S_3$ is proportional to the rotational speed of the engine, the output signal of this frequency detector represents the engine speed. The processing circuit 56 derives an engine speed value from the output of this frequency detector. The fourth terminal 62 receives an air flow rate signal $S_4$ outputted by a conventional air flow meter (not shown). The voltage of the signal $S_4$ represents the rate of air flow into the combustion chambers of the engine. The fourth terminal 62 is connected to the I/O circuit 58 to transmit the air flow rate signal $S_4$ to the I/O circuit 58. The I/O circuit 58 includes an analog-to-digital converter for converting the analog signal $S_4$ into a corresponding digital signal, from which the processing circuit 56 derives an air flow rate value. The fifth terminal 64 receives an engine coolant temperature signal $S_5$ outputted by a well-known engine coolant temperature sensor (not shown). The voltage of the temperature signal $S_5$ represents the temperature of engine coolant. The fifth terminal 64 is connected to the I/O circuit 58 to transmit the temperature signal $S_5$ to the I/O circuit 58. The I/O circuit 58 includes an analog-to-digital converter for converting the analog signal $S_5$ into a corresponding digital signal, from which the processing circuit 56 derives an engine coolant temperature value.

The control circuit 22 includes a sixth terminal 66. The microcomputer unit 54 generates a fuel injection pulse signal $S_6$ on the basis of the signals $S_1$, $S_3$, $S_4$, and $S_5$ indicating operating conditions of the engine. The fuel injection signal $S_6$ is outputted via the I/O circuit 58, which is connected to the terminal 66 to transmit the signal $S_6$ to the terminal 66. The terminal 66 is in turn connected to a fuel injection solenoid valve or valves (not shown) to apply the fuel injection signal $S_6$ to the valve or valves. Each pulse of the fuel injection signal $S_6$ causes the fuel injection valve or valves to open to supply fuel to the engine, so that the width of each pulse of the signal $S_6$ determines the length of time during which the fuel injection valve or valves are open. According to a conventional method, the microcomputer unit 54 generates pulses of the fuel injection signal $S_6$ at a predetermined engine crank-angle or crank-angles on the basis of the crank-angle signal $S_3$, so that the frequency of these pulses of the signal $S_6$ is proportional to the engine rotational speed. To control the rate of fuel injection that in turn determines the mixture air-to-fuel ratio, the microcomputer unit 54 adjusts the pulse width of the fuel injection signal $S_6$. The longer the pulse width of the fuel injection signal $S_6$, the richer the mixture. The shorter the pulse width of the signal $S_6$, the leaner the mixture.

Figure 3:
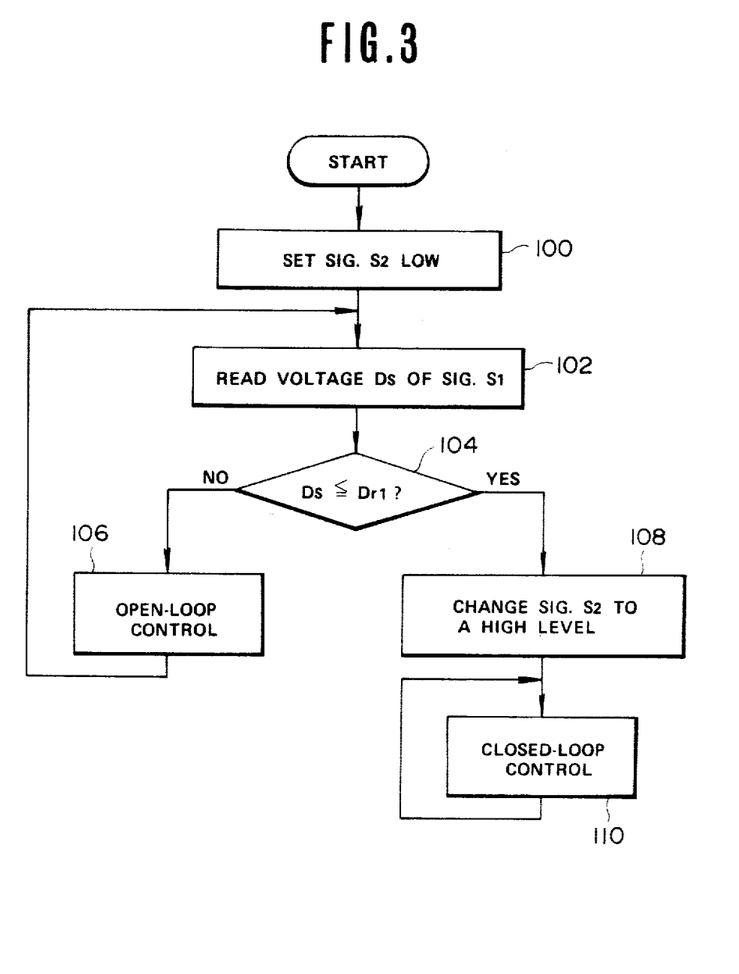
FIG. 3 is a flowchart of operation of the microcomputer unit in FIG. 1.

The microcomputer unit 54 operates in accordance with a program stored in the ROM of the processing unit 56. FIG. 3 is a flowchart of operation of the microcomputer unit 54. When an engine ignition switch (not shown) is turned on to start the engine, the microcomputer unit 54 commences its operation. In a first step 100 for initialization, the microcomputer unit 54 sets the signal $S_2$ low. As a result, the transistor 40 is initially nonconductive. In this case, the voltage $V_2$ across the resistor 38 is higher than the voltage $V_1$ across the resistor 32 applied to the series combination of the sensing element 12 and the thermistor 14, and this voltage $V_2$ is supplied across the series combination of the thermistor 14 and the resistor 44. Under these conditions, the voltage Es across the thermistor 14 depends mainly on the voltage $V_2$ and on the ratio of the resistances of the thermistor 14 and the resistor 44, so that this voltage Es decreases in accordance with decreases in the internal resistance of the thermistor 14 resulting from increases in the temperature of the oxygen sensor 10.

Figure 4:
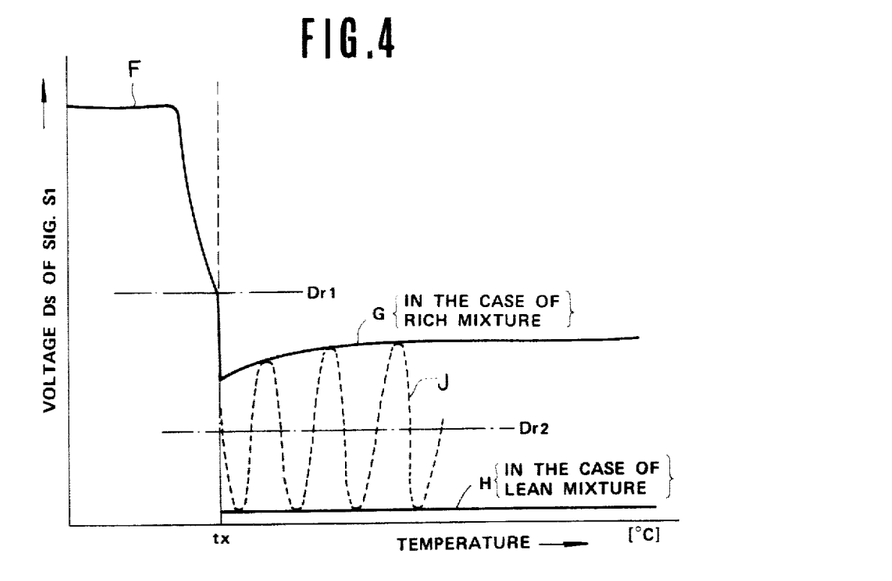
FIG. 4 is a diagram showing the relationship between the voltage of the signal from the amplifier and the temperature of the oxygen sensor in FIG. 1.

After the step 100, the microcomputer unit 54 reads the current level of the voltage Ds of the signal $S_1$ in a step 102. As shown by the curve B of FIG. 2, the internal resistance of the thermistor 14 drops with increases in the temperature of the oxygen sensor 10. The voltage Es across the thermistor 14 reflects the reduction of its internal resistance as described previously. Thus, the voltage Es drops as the temperature of the oxygen sensor 10 rises. Since the voltage Ds of the signal $S_1$ is proportional to the voltage Es, the voltage Ds drops with increases in the temperature of the oxygen sensor 10 as shown in FIG. 4 by the solid line F in the temperature range of up to a value tx. In this way, this voltage Ds indicates the temperature of the oxygen sensor 10.

In a step 104 subsequent to the step 102, the microcomputer unit 54 determines whether or not the value of the voltage Ds from the preceding step 102 is greater than a predetermined reference level $Dr_1$. If the value of the voltage Ds is greater than the reference level $Dr_1$, operation of the microcomputer unit 54 proceeds to an open-loop control step 106. If the value of the voltage Ds is equal to or less than the reference level $Dr_1$, operation of the microcomputer unit 56 proceeds to a step 108.

In the open-loop control step 106, the microcomputer unit 54 adjusts the pulse width of the fuel injection signal $S_6$ in response to the current values of the engine speed, the air-flow rate, and the engine coolant temperature derived from the signals $S_3$, $S_4$, and $S_5$. After the step 106, operation of the microcomputer unit 54 returns to the step 102. Thus, the sequence of the steps 102, 104, and 106 repeats cyclically and therefore open-loop control of the mixture air-to-fuel ratio continues as long as the voltage Ds is greater than the reference level $Dr_1$.

The oxygen sensor 10 is active or operative at temperatures higher than a certain critical level, but inactive or inoperative otherwise due to the extremely-high internal resistance of the sensing element 12. The reference level $Dr_1$ is chosen so as to represent a temperature value equal to or slightly higher than this critical level. Therefore, the voltage Ds being higher than the reference level $Dr_1$ essentially indicates that the temperature of the oxygen sensor 10 is in the inactive or inoperative range. The voltage Ds being equal to or less than the reference level $Dr_1$ indicates that the temperature of the oxygen sensor 10 is in the active or operative range. Since the sequence of the steps 102, 104, and 106 repeats cyclically as long as the voltage Ds is greater than the reference level $Dr_1$, open-loop control of the mixture air-to-fuel ratio continues while the temperature of the oxygen sensor 10 remains within the inoperative range.

Upon starting a normally cold engine, the temperature of the oxygen sensor 10 is considerably lower than the critical level so that open-loop control of the mixture air-to-fuel ratio is performed. Since operation of the engine generates hot exhaust gases, the temperature of the oxygen sensor 10 rises as the engine operates. In accordance with this temperature increase of the oxygen sensor 10, the voltage Ds drops as shown in FIG. 4 by the solid curve F up to a temperature point tx which corresponds to the voltage reference level $Dr_1$. Until the voltage Ds reaches the reference level $Dr_1$, that is, until the temperature of the oxygen sensor 10 reaches the operative range, open-loop control of the mixture air-to-fuel ratio continues. When the voltage Ds reaches the reference level $Dr_1$, open-loop control of the mixture air-to-fuel ratio is terminated and closed-loop control thereof is started instead as described hereinafter.

As described previously, operation of the microcomputer unit 54 proceeds to the step 108 of FIG. 3 when the voltage Ds is equal to or less than the reference level $Dr_1$. In this step 108, the microcomputer unit 54 changes the signal $S_2$ to a high level. The change of the signal $S_2$ to a high level switches the transistor 40 to a conductive state whereupon the resistor 38 is short-circuited. Short-circuiting the resistor 38 causes the voltages Es across the thermistor 14 to depend on the ratio of the internal resistances of the sensing element 12 and the thermistor 14 which represents the oxygen concentration in the exhaust gas, as described hereinafter in more detail. When the resistor 38 is short-circuited, the voltage thereacross drops essentially to zero so that the voltage Es across the thermistor 14 also drops considerably. This drop in the voltage Es causes the voltage Ds to decrease as shown in FIG. 4 by the solid line F at the temperature point tx.

In a closed-loop control step 110 subsequent to the step 108, the microcomputer unit 54 adjusts the pulse width of the fuel injection signal $S_6$ on the basis of the voltage Ds of the signal $S_1$. The microcomputer unit 54 repeats this step 110 cyclically, so that closed-loop control of the mixture air-to-fuel ratio continues without interruption until the engine is again turned-off.

In accordance with the sequence of the steps 104, 108, and 110, when the temperature of the oxygen sensor 110 rises to the operative range, that is, when the voltage Dr drops to the reference level $Dr_1$ as a result of sustained operation of the engine, the signal $S_2$ goes high and closed-loop control of the mixture air-to-fuel ratio is initiated to replace open-loop control thereof. Cyclical execution of the step 110 causes closed-loop control of the mixture air-to-fuel ratio to continue as long as the engine operates.

Figure 5:
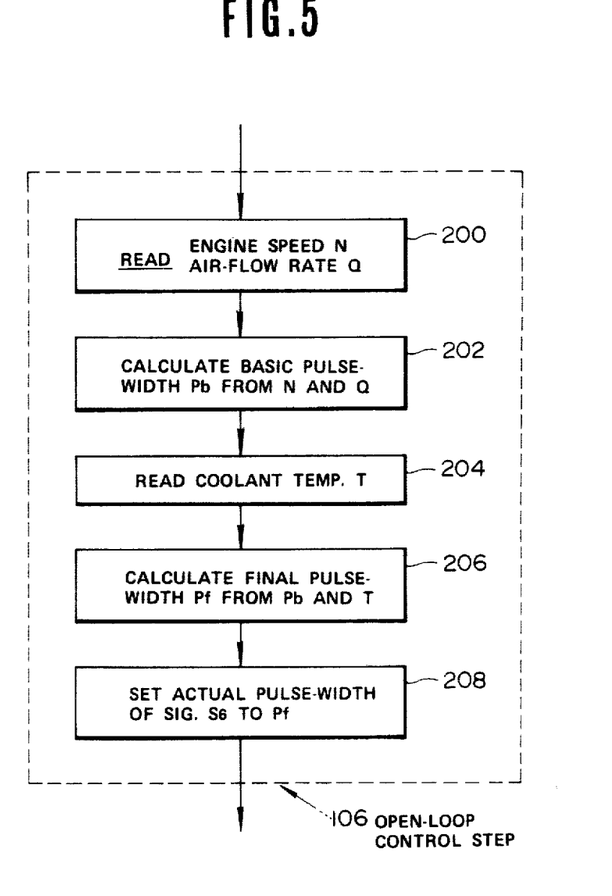
FIG. 5 illustrates the details of the open-loop control step of FIG. 3.

FIG. 5 illustrates the open-loop control step 106 in more detail. In a first block 200 of this step 106, the microcomputer unit 56 reads the current values of the engine speed N and the air-flow rate Q derived from the signals $S_3$ and $S_4$. After the block 200, operation of the microcomputer unit 56 proceeds to a block 202 in which the microcomputer unit 54 calculates a desired basic value Pb of fuel injection pulse-width on the basis of the engine speed value N and the air-flow rate value Q. In a block 204 subsequent to the block 202, the microcomputer unit 54 reads the current value of the engine coolant temperature T derived from the signal $S_5$. Then, the microcomputer unit 54 calculates a desired final value Pf of fuel injection pulse-width on the basis of the desired basic pulse-width value Pb and the engine temperature value T in a block 206 subsequent to the block 204. Specifically, the desired final pulse-width value Pf increases as the engine coolant temperature value T decreases. In a block 208 subsequent to the block 206, the microcomputer unit 54 sets the actual pulse-width of the fuel injection signal $S_6$ equal to the desired final pulse-width value Pf given in the preceding block 206. The open-loop control step 106 ends at this block 208.

To maintain the mixture air-to-fuel ratio at a constant level under varying engine operating conditions, the duty cycle of the fuel injection pulse signal $S_6$ which determines the rate of fuel injection needs to be held proportional to the air flow rate. Since the frequency of the fuel injection pulse signal $S_6$ is proportional to the engine speed as described previously, the desired pulse-width of the signal $S_6$ is determined on the basis of the engine speed and the air-flow rate, as described in the block 202, in order to keep the duty cycle of the fuel injection pulse signal $S_6$ proportional to the air flow rate.

Figure 6:
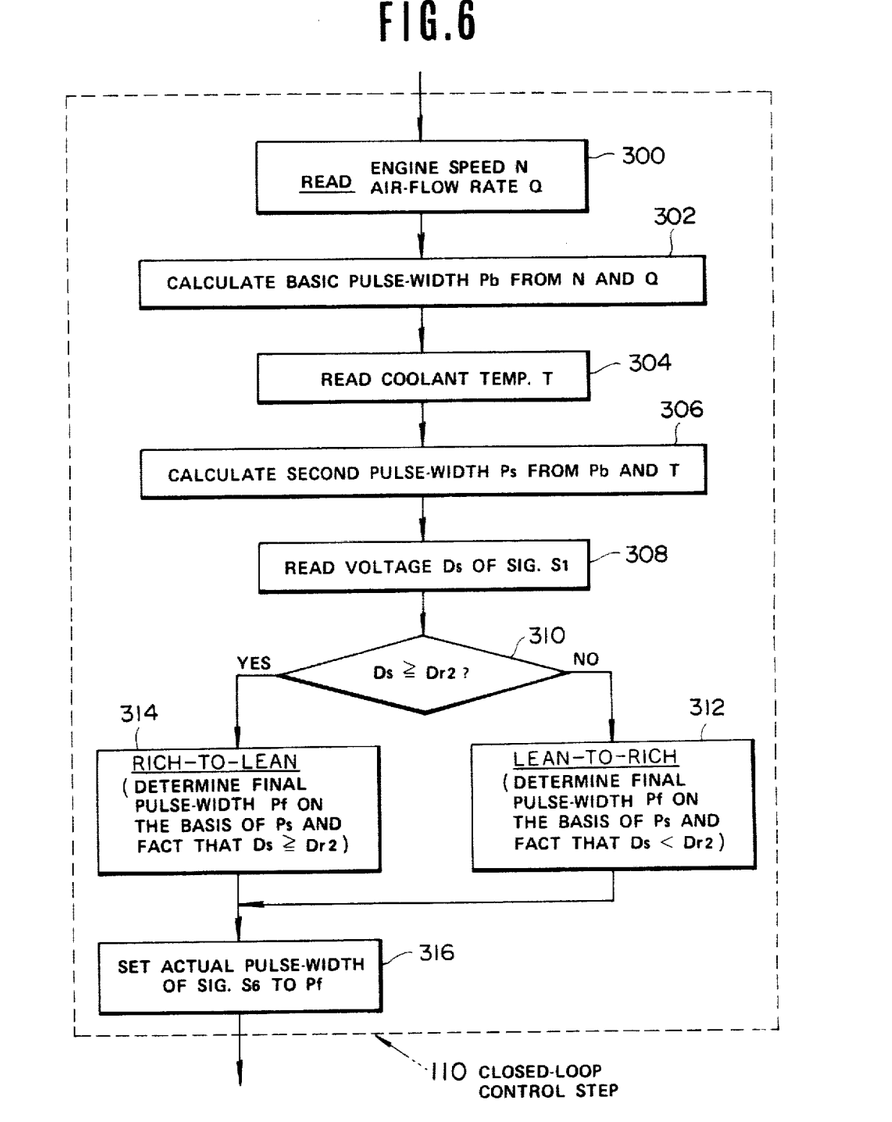
FIG. 6 illustrates the details of the closed-loop control step of FIG. 3.

FIG. 6 illustrates the closed-loop control step 110 in more detail. In a first block 300 of this step 110, the microcomputer unit 54 reads the current values of the engine speed N and the air-flow rate Q derived from the signals $S_3$ and $S_4$. After the block 300, operation of the microcomputer unit 54 proceeds to a block 302 in which the microcomputer unit 54 calculates a desired basic value Pb of fuel injection pulse-width on the basis of the engine speed value N and the air-flow rate value Q. In a block 304 subsequent to the block 302, the microcomputer unit 54 reads the current value of the engine coolant temperature T derived from the signal $S_5$. Then, the microcomputer unit 54 calculates a desired second value Ps of fuel injection pulse-width on the basis of the desired basic pulse-width value Pb and the engine temperature value T in a block 306 subsequent to the step 304. These blocks 300, 302, 304, and 306 are similar to the blocks 200, 202, 204, and 206 of the open-loop control step 106 (see FIG. 5), respectively. In a block 308 subsequent to the block 306, the microcomputer unit 54 reads the current level of the voltage Ds of the signal $S_1$. After the block 308, operation of the microcomputer unit 54 proceeds to a block 310 in which the microcomputer unit 54 determines whether or not the value of the voltage Ds given in the preceding block 310 is smaller than a predetermined reference level $Dr_2$. If the value of the voltage Ds is smaller than the reference level $Dr_2$, operation of the microcomputer unit 54 proceeds to a lean-to-rich block 312. If the value of the voltage Ds is equal to or greater than the reference level $Dr_2$, operation of the microcomputer unit 54 proceeds to a rich-to-lean block 314.

Figure 2:
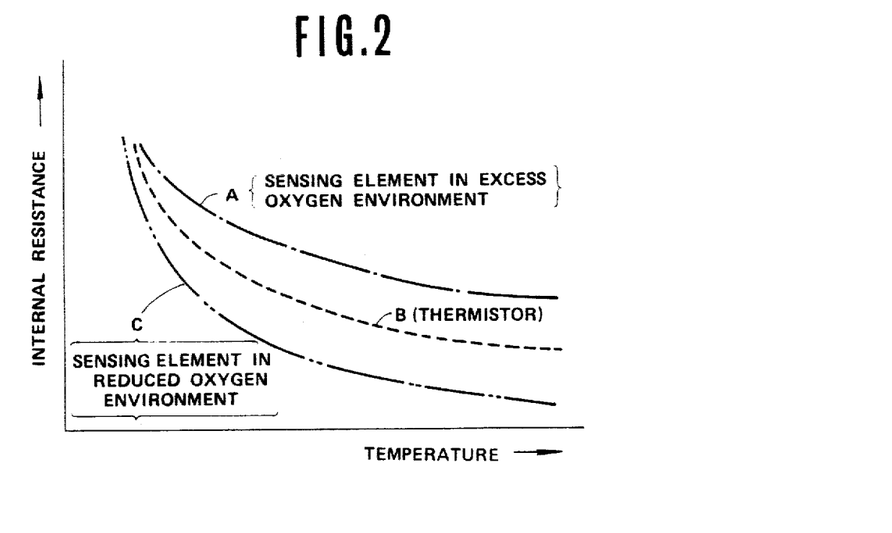
FIG. 2 is a graph showing the relationship between the internal resistance and the temperature of the sensing element and that between the internal resistance and the temperature of the thermistor of FIG. 1.

The resistor 38 has been short-circuited as a result of operation of the microcomputer unit 54 in the previous step 108 (see FIG. 3) where the signal $S_2$ was changed to a high level. While the resistor 38 remains short-circuited, the voltage Es across the thermistor 14 depends mainly on the voltage $V_1$ across the resistor 32 and also on the ratio of the internal resistances of the sensing element 12 and the thermistor 14. This internal-resistance ratio is essentially independent of the temperature of the oxygen sensor 10 as described previously. As shown in FIG. 2, the internal resistance of the sensing element 12 exposed to exhaust gases resulting from an air/fuel mixture leaner than stoichiometric (denoted by the line A) is considerably greater than that exposed to exhaust gases resulting from an air/fuel mixture richer than stoichiometric (denoted by the line C) at equal temperatures of the oxygen sensor 10. Thus, the ratio of the internal resistances of the sensing element 12 and the thermistor 14 sensitively depends on whether the air/fuel mixture is rich or lean with respect to stoichiometry. Accordingly, the voltage Es across the thermistor 14 is independent of the temperature of the oxygen sensor 10 but sensitively depends on whether the air/fuel mixture is rich or lean. Since the voltage Ds of the signal $S_1$ is proportional to this voltage Es, the voltage Ds is independent of the temperature of the oxygen sensor 10 but varies as a function of the richness or leanness of the air/fuel mixture. In this way, the temperature compensation is realized and the mixture air-to-fuel ratio is sensed.

As shown in FIG. 4, the voltage Ds in the case of rich air/fuel mixture (denoted by the solid line G starting from the temperature point tx) is considerably greater than that in the case of lean air/fuel mixture (denoted by the solid line H starting from the point tx). The voltage Ds in the case of lean air/fuel mixture remains accurately constant at temperatures of the oxygen sensor 10 higher than the point tx as a result of the temperature compensation due to advantageous use of the thermistor 14. The voltage Es in this case is roughly zero, since the internal resistance of the thermistor 14 will be significantly lower than that of the sensing element 12 as is apparent from FIG. 2. Also, the voltage Ds in the case of rich air/fuel mixture remains substantially constant at temperatures higher than the point tx. The voltage Es in this case will be roughly equal to the voltage $V_1$ across the resistor 32, since the internal resistance of the thermistor 14 is significantly greater than that of the sensing element 12 as is apparent from FIG. 2. The reference level $Dr_2$ used in the block 310 (see FIG. 6) is chosen to lie between the levels of the voltage Ds in the cases of rich and lean air/fuel mixture, and preferably to be substantially centered between these levels as shown in FIG. 4. Therefore, the voltage Ds being smaller than the reference level $Dr_2$ indicates that the air/fuel mixture is leaner than stoichiometric, while the voltage Ds being equal to or greater than the reference level $Dr_2$ indicates that the air/fuel mixture is richer than stoichiometric.

If the value of the voltage Ds is smaller than the reference level $Dr_2$, that is, if the air/fuel mixture is lean, operation of the microcomputer unit 54 proceeds from the block 310 to the lean-to-rich block 312 as described previously. In this block 312, the microcomputer unit 54 determines or calculates a desired final value Pf of fuel injection pulse-width on the basis of the desired second pulse-width value Ps given in the previous block 306 and the fact that the air/fuel mixture is lean, as determined in the preceding block 310. In addition, the desired final pulse-width value Pf given in this block 312 is designed to increase the actual pulse-width of the fuel injection signal $S_6$ in order to enrich the air/fuel mixture.

If the value of the voltage Ds is equal to or greater than the reference level $Dr_2$, that is, if the air/fuel mixture is rich, operation of the microcomputer unit 54 proceeds from the block 310 to the rich-to-lean block 314 as described previously. In this block 314, the microcomputer unit 54 determines or calculates a desired final value Pf of fuel injection pulse-width on the basis of the desired second pulse-width value Ps given in the previous block 306 and the fact that the air/fuel mixture is rich, as determined in the preceding block 310. In addition, the desired final pulse-width value Pf given in this block 314 is designed to decrease the actual pulse-width of the fuel injection signal $S_6$ in order to make the air/fuel mixture leaner.

In a block 316 subsequent to the blocks 312 and 314, the microcomputer unit 54 sets the actual pulse-width of the fuel injection signal $S_6$ equal to the desired final pulse-width value Pf given in the preceding block 206. The closed-loop control step 110 ends at this block 316.

Since the closed-loop control step 110 repeats cyclically as described previously, the air/fuel mixture is maintained near or at stoichiometry under varying engine operating conditions by means of closed-loop control. As shown by the broken curve J of FIG. 4, the voltage Ds of the signal $S_1$ tends to cycle between the levels denoted by the lines G and H due to this closed-loop control as the temperature of the oxygen sensor 10 rises in accordance with sustained engine operation.

Normally, once the engine, and thus the oxygen sensor 10, have warmed up, they will remain within a range of temperature well above the critical temperature of the sensing element 12. In view of the fact, once closed-loop control is initiated, the system does not again check the temperature of the oxygen sensor 10.

As apparent from the above-mentioned overall operation of the control circuit 22, the transistor 40 and the associated resistor network allow the oxygen sensor 10 to be used in either of two modes. When the transistor 40 is nonconductive, the voltage Es across the thermistor 14 reflects the ratio of the resistances of the thermistor 14 and the resistor 44 so that the signal $S_1$ indicates the temperature of the oxygen sensor 10. When the transistor 40 is conductive, the voltage Es across the thermistor 14 reflects the ratio of the resistances of the thermistor 14 and the sensing element 12 so that the signal $S_1$ indicates the mixture air-to-fuel ratio.

Figure 7:
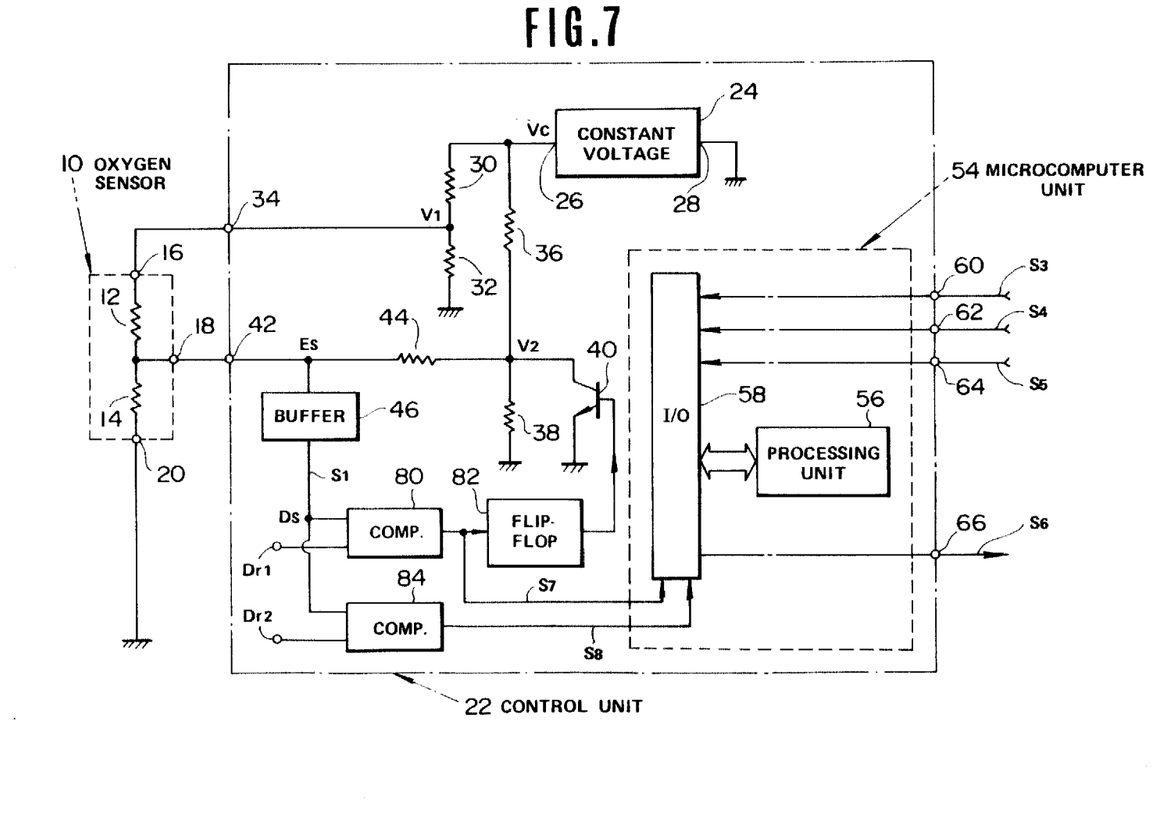
FIG. 7 is a schematic diagram of an oxygen-sensing system according to a second embodiment of this invention.

FIG. 7 diagrammatically illustrates a second embodiment of this invention. In this embodiment, the voltage Es across the thermistor 14 is transmitted to a first input terminal of a first comparator 80 through a buffer 46. The output signal $S_1$ from the buffer 46 has a voltage Ds which equals the voltage Es across the thermistor 14. A first predetermined reference voltage $Dr_1$ is applied to the second input terminal of the comparator 80. This comparator 80 serves to determine whether or not the voltage Ds of the signal $S_1$ exceeds the first reference voltage $Dr_1$. The first reference voltage $Dr_1$ is chosen so that the comparator 80 can determine whether or not the temperature of the oxygen sensor 10 is in the operative range. When the voltage Ds of the signal $S_1$ exceeds the first reference voltage $Dr_1$, that is, when the temperature of the oxygen sensor 10 is in the inoperative range, the output signal $S_7$ from the comparator 80 is low in voltage. When the voltage Ds of the signal $S_1$ drops to the first reference voltage $Dr_1$, that is, when the temperature of the oxygen sensor 10 rises to the operative range, the output signal $S_7$ from the comparator 80 goes high in voltage.

A flip-flop (F/F) circuit 82 has a set terminal, which is connected to the output terminal of the comparator 80 to receive the signal $S_7$. The output terminal of the F/F circuit 82 is connected to the base of the transistor 40, so that the output signal from the F/F circuit 82 is applied to the base of the transistor 40. As the output signal from the F/F circuit 82 switches between a low level and a high level, the transistor 40 is rendered nonconductive and conductive respectively. The output signal from the F/F circuit 82 is initially low in voltage. In other words, the output signal from the F/F circuit 82 is low just when or immediately after the engine ignition switch is turned on. Since the low output signal applied from the F/F cuircuit 82 to the base of the transistor 40 causes the transistor 40 to be nonconductive, the transistor 40 is initially nonconductive. A low-level to high-level change of the output signal $S_7$ from the comparator 80 triggers the F/F circuit 82 to switch from a low-level output to a high-level output. When the voltage Ds of the signal $S_1$ drops to the first reference level $Dr_1$ so that the output signal $S_7$ from the comparator 80 goes high, the output signal from the F/F circuit 82 is driven high and thus the transistor 40 is changed to the conductive state. In this way, the transistor 40 is rendered conductive to short-circuit the resistor 38 when the temperature of the oxygen sensor 10 enters the operative range.

The I/O circuit 58 of the microcomputer unit 54 is connected to the output terminal of the comparator 80 to receive the signal $S_7$ as an indication of whether or not the oxygen sensor 10 is inoperative.

A second comparator 84 has a first input terminal, which is connected to the output terminal of the buffer 46 to receive the voltage Ds of the signal $S_1$. The second input terminal of the comparator 84 is supplied with a second predetermined reference voltage $Dr_2$. The comparator 84 serves to determine whether or not the voltage Ds of the signal $S_1$ exceeds the second reference voltage $Dr_2$. The second reference voltage $Dr_2$ is chosen so that the comparator 84 can determine whether the air/fuel mixture is rich or lean. Specifically, the output signal $S_8$ from the comparator 84 assumes a low level and a high level when the air/fuel mixture is rich and lean respectively.

The I/O circuit 58 of the microcomputer unit 54 is connected to the output terminal of the comparator 84 to receive the signal $S_8$ as an indication of whether the air/fuel mixture is rich or lean.

Other parts of this second embodiment except the microcomputer unit 54 are designed in a manner similar to those of the first embodiment, so that their description will be omitted.

Figure 8:
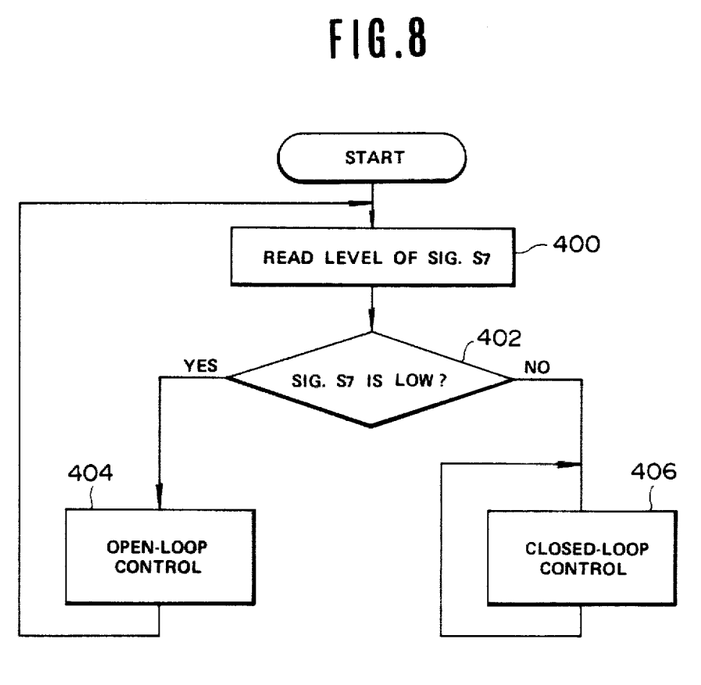
FIG. 8 is a flowchart of operation of the microcomputer unit in FIG. 7.

FIG. 8 is a flowchart of operation of the microcomputer unit 54 of this second embodiment. In a first step 400 initiated by turning on the engine ignition switch (not shown), the microcomputer unit 54 reads the level of the signal $S_7$ outputted by the first comparator 80. In a step 402 subsequent to the step 400, the microcomputer unit 54 determines whether the level of the signal $S_7$ is high or low. If the level of the signal $S_7$ given in the preceding step 400 is low, operation of the microcomputer unit 54 proceeds to an open-loop control step 404. If the level of the signal $S_7$ is high, operation of the microcomputer unit 54 proceeds to a closed-loop control step 406.

In the step 404, the microcomputer unit 54 adjusts the pulse width of the fuel injection signal $S_6$ in response to current values of the engine speed, the air-flow rate, and the engine coolant temperature derived from the signals $S_3$, $S_4$, and $S_5$. The detailed actions taken in the step 404 are identical to those of the step 106 (see FIGS. 3 and 5) of the first embodiment, so that description thereof will be omitted. After the step 404, operation of the microcomputer unit 54 returns to the step 400. Thus, the sequence of the steps 400, 402, and 404 is cyclically repeated as long as the level of the signals $S_7$ remains low. Since the output signal from the F/F circuit 82 to the transistor 40 is initially low, the signal $S_1$ generally indicates at first the temperature of the oxygen sensor 10, not the mixture air/fuel ratio. Upon starting a normally cold engine, the temperature of the oxygen sensor 10 is in the inoperative range so that the level of the signal $S_7$ is low. The sequence of the steps 400, 402, and 404 is cyclically repeated until the temperature of the oxygen sensor 10 rises to the operative range, that is, until the level of the signal $S_7$ goes high. In this way, open-loop control of the mixture air-to-fuel ratio commences simultaneously with engine start-up and generally continues while the temperature of the oxygen sensor 10 remains in the inoperative range.

When the signal $S_7$ goes high, that is, when the temperature of the oxygen sensor 10 rises into the operative range, the output signal from the F/F circuit 82 to the transistor 40 is driven high so that the transistor 40 changes to the conductive state in which the resistor 38 is short-circuited. As a result, the signal $S_1$ starts to accurately indicate the mixture air/fuel ratio rather than the temperature of the oxygen sensor 10. When the signal $S_7$ goes high, operation of the microcomputer unit 54 proceeds from the step 402 to the closed-loop control step 406. In this step 406, the microcomputer unit 54 adjusts the pulse width of the fuel injection signal $S_6$ on the basis of the level of the output signal $S_8$ from the second comparator 84 which represents whether the air/fuel mixture is rich or lean. The microcomputer unit 54 cyclically repeats the step 406. As a result of cyclical repetition of the step 406, the mixture air/fuel ratio is held near or at stoichiometry by means of closed-loop control, which continues after the temperature of the oxygen sensor 10 enters the operative range.

Figure 9:
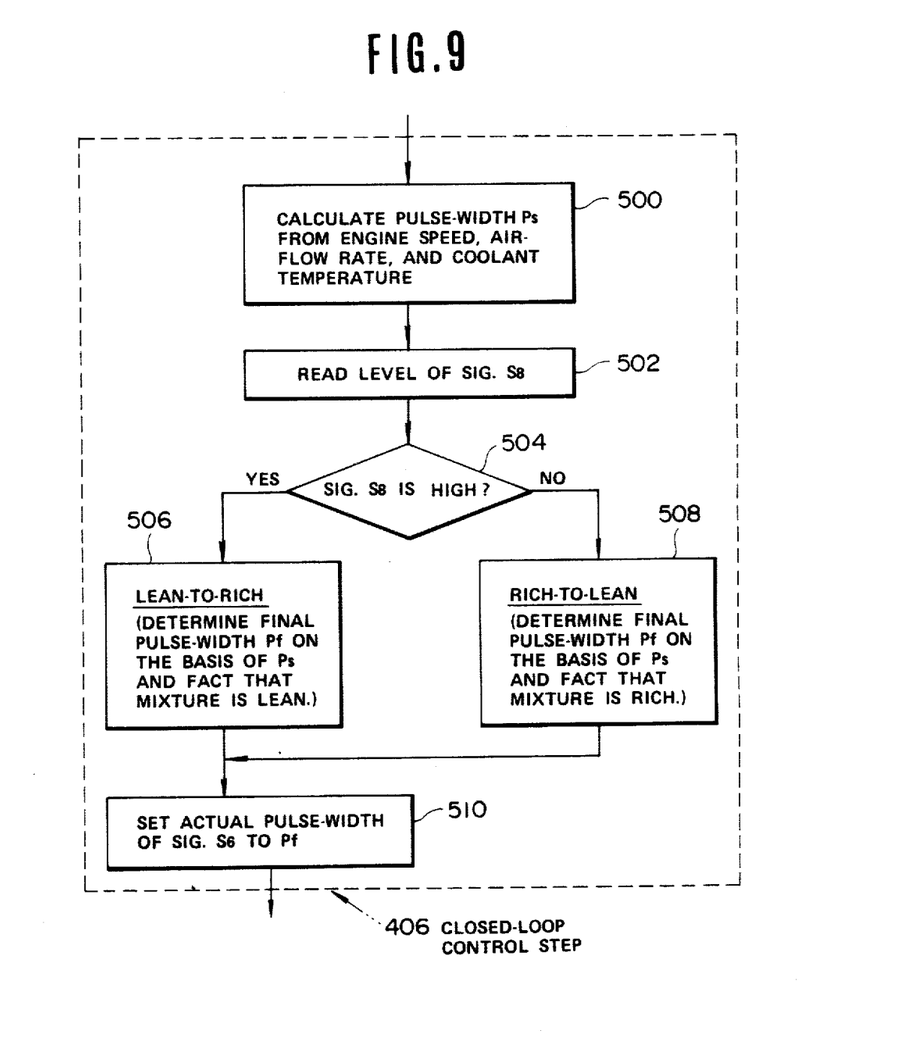
FIG. 9 illustrates the details of the closed-loop control step of FIG. 8.

FIG. 9 illustrates the details of the closed-loop control step 406. In a first block 500 of this step 406, the microcomputer unit 54 reads the current values of the engine speed N, the air-flow rate Q, and the engine coolant temperature T derived from the signals $S_3$, $S_4$, and $S_5$ and also determines or calculates a desired second value Ps of fuel injection pulse-width on the basis of the engine speed value N, the air-flow rate value Q, and the engine coolant temperature value T. The specific actions to perform the functions of this block 500 are identical to those of the series of the blocks 300, 302, 304, and 306 in the closed-loop control step 110 (see FIGS. 3 and 6) of the first embodiment, so that detailed description thereof will be omitted. In a block 502 subsequent to the block 500, the microcomputer unit 54 reads the level of the signal $S_8$ from the second comparator 84. Note that the level of this signal $S_8$ represents whether the air/fuel mixture is rich or lean. In a block 504 subsequent to the block 502, the microcomputer unit 54 determines whether the level of the signal $S_8$ is high or low. If the level of the signal $S_8$ is high, that is, if the air/fuel mixture is lean, operation of the microcomputer unit 54 proceeds from the block 504 to a lean-to-rich block 506. If the level of the signal $S_8$ is low, that is, if the air/fuel mixture is rich, operation of the microcomputer unit 54 proceeds from the block 504 to a rich-to-lean block 508.

In the lean-to-rich block 506, the microcomputer unit 54 determines or calculates desired final value Pf of fuel injection pulse-width on the basis of the desired second pulse-width value Ps given in the previous block 500 and the fact that the air/fuel mixture is lean, as determined in the preceding block 504. This block 506 is identical to the block 312 in the closed-loop control step 110 of the first embodiment (see FIGS. 3 and 6), and thus acts to enrich the air/fuel mixture. In the rich-to-lean block 508, the microcomputer unit 54 determines or calculates a desired final value Pf of fuel injection pulse-width on the basis of the desired second pulse-width value Ps given in the previous block 500 and the fact that the air/fuel mixture is rich, as determined in the preceding block 504. This block 508 is identical to the block 314 in the closed-loop control step 110 (see FIGS. 3 and 6), and thus acts to make the air/fuel mixture leaner. After the blocks 506 and 508, operation of the microcomputer unit 54 proceeds to a block 510 in which the microcomputer unit 54 sets the actual pulse-width of the fuel injection signal $S_6$ equal to the desired final pulse-width value Pf given in the preceding blocks 506 and 508. The closed-loop control step 406 ends at this block 510.

In a modification of the first embodiment, the first terminal 16 of the oxygen sensor 10 may be grounded. In this case, the third terminal 20 should be connected to the first terminal 34 of the control circuit 22. In this modification, the voltage across the sensing element 12 is used as an indication of the temperature of the oxygen sensor 10 and the mixture air-to-fuel ratio. The reference levels $Dr_1$ and $Dr_2$ should be chosen in view of this fact.

What is claimed is:

1. An oxygen-sensing system comprising:

(a) a sensing element exposed to a gas to be analyzed for oxygen concentration, the sensing element having an internal electrical resistance which depends on its temperature and also on the oxygen concentration in the gas;

(b) a thermistor having an internal electrical resistance which depends on its temperature, the thermistor being positioned near the sensing element so that the temperature of the thermistor substantially coincides with the temperature of the sensing element, the ratio of the internal resistances of the thermistor and the sensing element being substantially independent of the temperature of the thermistor and the sensing element but being dependent on the oxygen concentration in the gas;

(c) first means for sensing the internal resistance of the thermistor and thereby determining the temperature of the sensing element;

(d) second means for sensing the ratio of the internal resistances of the thermistor and the sensing element and thereby determining the oxygen concentration in the gas;

(e) means, responsive to the first means, for generating a first signal indicative of the temperature of the sensing element;

(f) means for generating a second signal indicative of a predetermined reference level for the temperature of the sensing element;

(g) means, responsive to the first and second signals, for determining whether or not the temperature of the sensing element is lower than the reference level and generating a third signal indicative thereof; and (h) means, responsive to the third signal, for enabling the first means and disabling the second means when the temperature of the sensing element is lower than the reference level, and for enabling the second means and disabling the first means when the temperature of the sensing element rises to the reference level.

2. The system of claim 1, further comprising:
(a) means for generating a fourth signal indicative of a predetermined reference value for the oxygen concentration in the gas; and
(b) means, responsive to the first and fourth signals, for determining whether or not the oxygen concentration in the gas exceeds the reference value.

3. An oxygen-sensing system comprising:
(a) a sensing element exposed to a gas to be analyzed for oxygen concentration, the sensing element having an internal electrical resistance which depends on its temperature and also on the oxygen concentration in the gas;
(b) a thermistor electrically connected in series with the sensing element, the thermistor having an internal electrical resistance which depends on its temperature, the thermistor being positioned near the sensing element so that the temperature of the thermistor substantially coincides with the temperature of the sensing element, the ratio of the internal resistances of the thermistor and the sensing element being substantially independent of the temperature of the thermistor and the sensing element but being dependent on the oxygen concentration in the gas;
(c) a fixed resistor electrically connected in series with the thermistor;
(d) first means for applying a first voltage across the series combination of the sensing element and the thermistor;

(e) second means for selectively applying a second voltage across the series combination of the thermistor and the resistor; and
(f) third means for sensing the voltage across the thermistor and generating a first signal indicative thereof.

4. The system of claim 3, further comprising:
(a) fourth means for generating a second signal indicative of a first reference level for the voltage across the thermistor;
(b) fifth means, responsive to the first and second signals, for determining whether or not the voltage across the thermistor exceeds the first reference level and generating a third signal indicative thereof;
(c) sixth means, responsive to the third signal, for enabling the second means to apply the second voltage across the series combination of the thermistor and the resistor when the voltage across the thermistor exceeds the first reference level and disabiling the second means from applying the second voltage across the series combination of the thermistor and the resistor when the voltage across the thermistor drops to the first reference level.
(d) seventh means for generating a fourth signal indicative of a second reference level for the voltage across the thermistor;
(f) eighth means, responsive to the first and fourth signals, for determining whether or not the voltage across the thermistor exceeds the second reference level.

5. A method of sensing the oxygen concentration in a gas by means of an oxygen sensor comprising a sensing element and a thermistor, the sensing element being exposed to the gas, the sensing element having an internal electrical resistance which depends on its temperature and also on the oxygen concentration in the gas, the thermistor being positioned near the sensing element so that the temperature of the thermistor coincides with the temperature of the sensing element, the thermistor having an internal electrical resistance which depends on its temperature, the ratio of the internal resistances of the sensing element and thermistor being substantially independent of the temperature of the sensing element and the thermistor but being dependent on the oxygen concentration in the gas, the method being applied to conditions where the temperature of the sensing element and the thermistor rises, the method comprising the steps of:
(a) measuring the internal resistance of the thermistor;
(b) deriving the temperature of the sensing element and the thermistor from the measured thermistor resistance;
(c) determining whether or not the derived temperature of the sensing element and the thermistor is lower than a predetermined reference level;
(d) when the derived temperature of the sensing element and the thermistor is lower than the reference level, cyclically repeating the series of the previous steps (a), (b) and (c);
(e) when the derived temperature of the sensing element and the thermistor is not lower than the reference level, measuring the ratio of the internal resistances of the sensing element and the thermistor; and
(f) deriving the oxygen concentration in the gas from the measured internal resistance ratio.

6. The method of claim 5, comprising the additional step of determining whether or not the derived oxygen concentration exceeds a predetermined reference level.

* * * * *